United States Patent [19]
Tumey et al.

[11] Patent Number: 5,991,654
[45] Date of Patent: Nov. 23, 1999

[54] APPARATUS AND METHOD FOR DETECTING DEEP VEIN THROMBOSIS

[75] Inventors: David M. Tumey; Larry Tab Randolph, both of San Antonio, Tex.

[73] Assignee: KCI New Technologies, Inc., San Antonio, Tex.

[21] Appl. No.: 08/870,232

[22] Filed: Jun. 6, 1997

[51] Int. Cl.⁶ ..................................................... A61B 5/02
[52] U.S. Cl. ........................ 600/479; 600/473; 600/504; 128/925
[58] Field of Search ..................................... 600/473, 480, 600/482, 485, 492, 504, 506, 507, 479, 408, 476, 310; 128/920, 925

[56] References Cited

U.S. PATENT DOCUMENTS

| | | |
|---|---|---|
| 3,847,142 | 11/1974 | Williams, Jr. et al. . |
| 4,569,355 | 2/1986 | Bitterly . |
| 4,574,812 | 3/1986 | Arkans . |
| 4,721,113 | 1/1988 | Stewart et al. . |
| 4,962,764 | 10/1990 | Matsumura . |
| 5,090,417 | 2/1992 | Mollan et al. . |
| 5,140,990 | 8/1992 | Jones et al. . |
| 5,241,963 | 9/1993 | Shankar . |
| 5,267,565 | 12/1993 | Beard . |
| 5,282,467 | 2/1994 | Piantedosi et al. ..................... 128/633 |
| 5,297,556 | 3/1994 | Shankar . |
| 5,343,867 | 9/1994 | Shankar . |
| 5,379,774 | 1/1995 | Nishimura et al. . |
| 5,417,220 | 5/1995 | Apple . |
| 5,447,163 | 9/1995 | Apple . |
| 5,590,649 | 1/1997 | Caro et al. . |
| 5,671,751 | 9/1997 | Tumey et al. . |
| 5,674,262 | 10/1997 | Tumey . |
| 5,680,857 | 10/1997 | Pelikan et al. . |
| 5,715,826 | 2/1998 | Horrocks et al. . |
| 5,715,828 | 2/1998 | Raines et al. . |
| 5,724,981 | 3/1998 | Apple . |
| 5,803,907 | 9/1998 | Patchett et al. . |
| 5,810,734 | 9/1998 | Caro et al. . |

FOREIGN PATENT DOCUMENTS 0208201  6/1986  European Pat. Off. .

OTHER PUBLICATIONS

Keates et al., Plethysmography: A new application for an intermittent compression unit, vol. 9, No. 4, Jul.–Aug. 1975.
Hubner, Is the Light Reflection Rheography (LRR) Suitable as a Diagnostic Method for the Phlebology Practice, Phlebology and Proctology 1986; 15:209–12.
McEnroe et al., Correlation of Clinical Findings With Venous Hemodynamics in 386 Patients With Chronic Venous Insufficiency, The American Journal of Surgery vol. 156 Aug. 1988.
Shepard et al., Light Reflective Rheology (LLR): A New Non–Invasive Test of Venous Function, Bruit, Dec. 1984.
Stemmer et al., Light Reflective Rheography and the Diagnosis of Thrombosis in the Deep Leg Veins, Phlebology—Jan.–Mar. 1984.
Blazek, Functional Diagnostics of Peripheral Vein Disorders A New Non–Invasive Method, Hautarzt—Oct. 1984.
Unknown Author, Impedence Plethysmography, Undated.

*Primary Examiner*—William E. Kamm
*Assistant Examiner*—Shawna J. Shaw
*Attorney, Agent, or Firm*—Wayne J. Colton, Inc.

[57] ABSTRACT

An apparatus for detecting Deep Vein Thrombosis (DVT) in a patient includes a computer based device, a device disposed on a predetermined position on a calf of the patient for measuring blood volume, another device for measuring temperature of the calf and still another device for measuring calf size. A cuff is operably connected to the computer based device and envelops a portion of a thigh of the patient and is controllably restrictable by the computer based device to produce a controlled venous occlusion of the patient's deep veins for a predetermined period. A method for detecting DVT using the device is also provided.

23 Claims, 9 Drawing Sheets

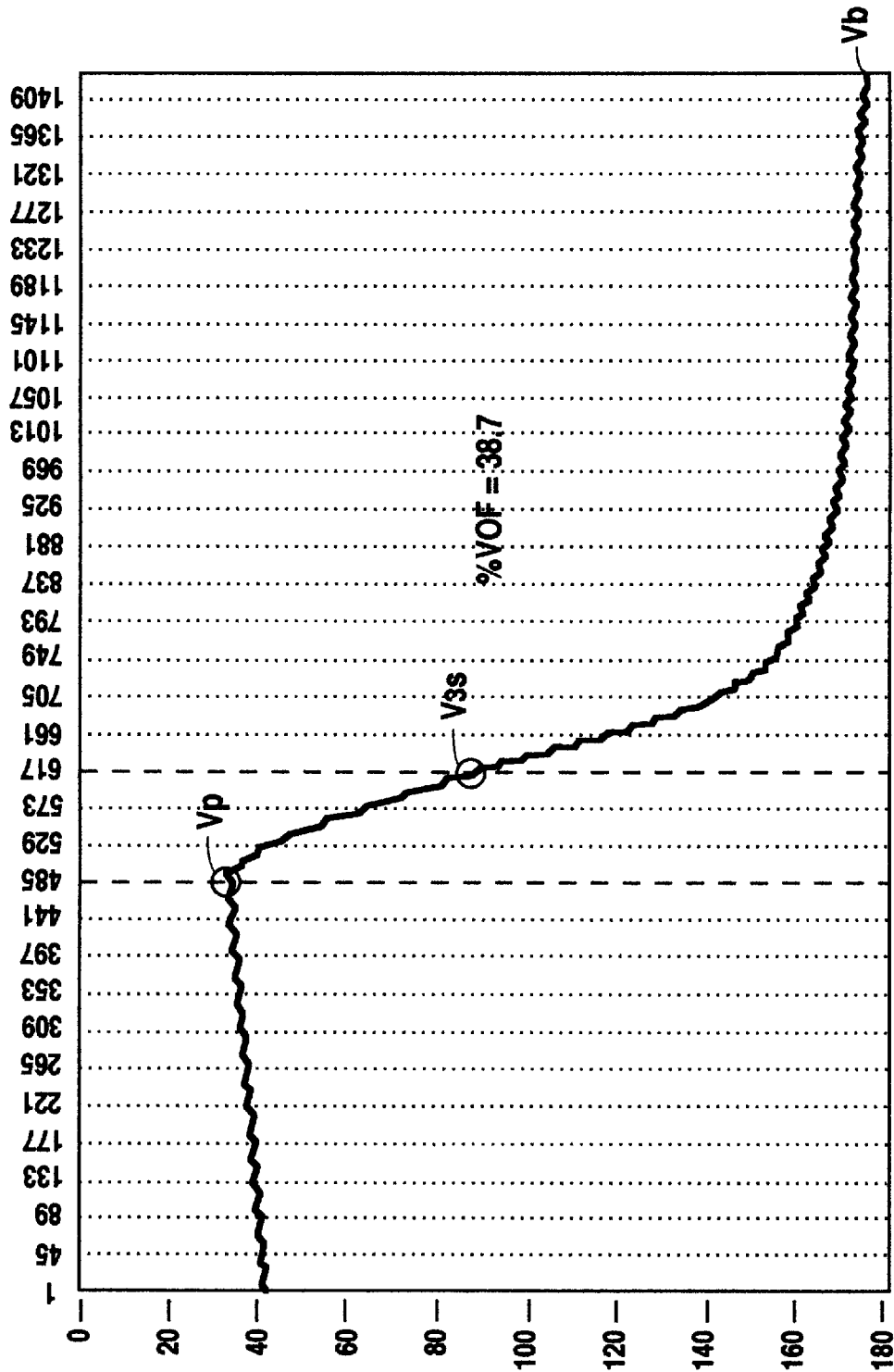

| | "HOMAN'S SIGN" | CALF CIRCUMFERENCE | BASELINE TEMP. Trb | MAX. VENOUS CAPACITY TEMP. Tvc | PERCENTAGE VENOUS OUTFLOW % Vof | MIN. VENOUS CAPACITY TEMP. Tve |
|---|---|---|---|---|---|---|
| LEFT LEG | 7 (0-10) | 40 cm | 37.8° C | 38.2° C | 38.7 % | 37.4° C |
| RIGHT LEG | 3 (0-10) | 37 cm | 36.1° C | 36.9° C | 92% | 35.8° C |

APPARATUS AND METHOD FOR DETECTING DEEP VEIN THROMBOSIS

BACKGROUND OF THE INVENTION

1. Field of the Invention

The present invention is generally directed to apparatus and method for detecting venous obstruction. More particularly, but not by way of limitation, the invention is directed to apparatus and method for detecting DVT in a patient by measuring blood volume, temperature, calf size and other clinical indications.

2. Related Art

There exist many methods for detection of obstruction in a human's circulatory system. Depending upon which part of the circulatory system is examined, a particular method may or may not lend itself as well to detecting obstructions. Methods employing invasive, i.e., surgical techniques, are a last resort due to their inherent severity and limitations in repeated use.

Non-invasive devices have hence been preferred in the diagnosis of venous obstruction. Ultrasonic devices have been used to study venous thrombosis in the deep veins, but are limited in that these require highly skilled operators, thus rendering subjective uncertainty in their resulting diagnosis.

Other devices measure arterial elasticity to determine whether sclerosis exists in the artery. Such devices have employed photoelectric plethysmography to monitor the change in transmitted light intensity across tissues, such as fingers, to diagnose sclerosis.

Still others have used inflatable cuffs which wrap about a limb and measure diastolic and systolic pressure to detect peripheral arterial disease. Others have coupled cuffs with impedance plethysmography to detect atherosclerosis. Also, there has been use of light reflective rheography on the ankle for detection of chronic venous insufficiency.

Although there exist various apparatuses and methods of detecting venous and arterial irregularity, there remains a great need to improve apparatuses and methods for the detection of DVT. Specifically, the existing devices which detect DVT by measuring venous outflow such as impedance plethysmography or strain-gauge plethysmography, are not consistent from patient to patient, require highly developed operator skill, and are unable to detect chronic proximal DVTs or acute/chronic distal DVTs. The present invention, through the use of multiple risk factor analysis and artificial intelligence algorithms is able to overcome the shortcomings of the prior art devices and provide a significantly improved apparatus for detecting DVT.

BRIEF SUMMARY OF THE INVENTION

It is an object of the present invention to improve the apparatus and method for detecting venous obstruction.

Another object of this invention is to improve the apparatus and method for detecting DVT.

Accordingly, one embodiment of the invention is directed to an apparatus for detecting DVT in a patient which includes a computer based device, at least one biocharacteristic gathering device operably associated with the computer based device, wherein one biocharacteristic gathering device is disposed on a predetermined position on a calf of the patient for measuring blood volume, a cuff operably connected to the computer based device and of a size and configuration to envelop a portion of a thigh of the patient and being controllably restrictable by the computer based device to produce a controlled venous occlusion of the patient's deep veins for a predetermined period. The apparatus further includes another biocharacteristic gathering device for measuring temperature and still another biocharacteristic gathering device for measuring calf size.

Another embodiment is directed to a method for detecting DVT in a patient. The method includes the steps of measuring and recording blood volume in a calf of the patient at predetermined time periods, applying pressure at one of the time periods to a portion of the patient's thigh in a manner to restrict deep and superficial veins in the leg to preclude blood flow therethrough, removing pressure at another of the time periods from the portion of the patient's thigh in a manner to relax deep and superficial veins in the leg to permit blood flow therethrough, and generating an output which is indicative of DVT as a function of blood volume in the calf over the predetermined periods. The method may further include measuring and storing temperature of the patient's calf at predetermined time periods. The method may further include measuring and storing the patient's calf size at predetermined time periods. The method may further include measuring and storing other clinical indications. Also, the method includes positioning the patient's leg at an angle relative to the patient's heart to permit blood flow freely from the distal deep and superficial venous system to the heart. The method is further characterized as using a computer based device to perform the steps of the invention.

Other objects and advantages will be readily apparent to those skilled in the art upon viewing the drawings and reading the detailed description hereafter.

FIG. I a shows an aspect of the present invention.

Figure 2:
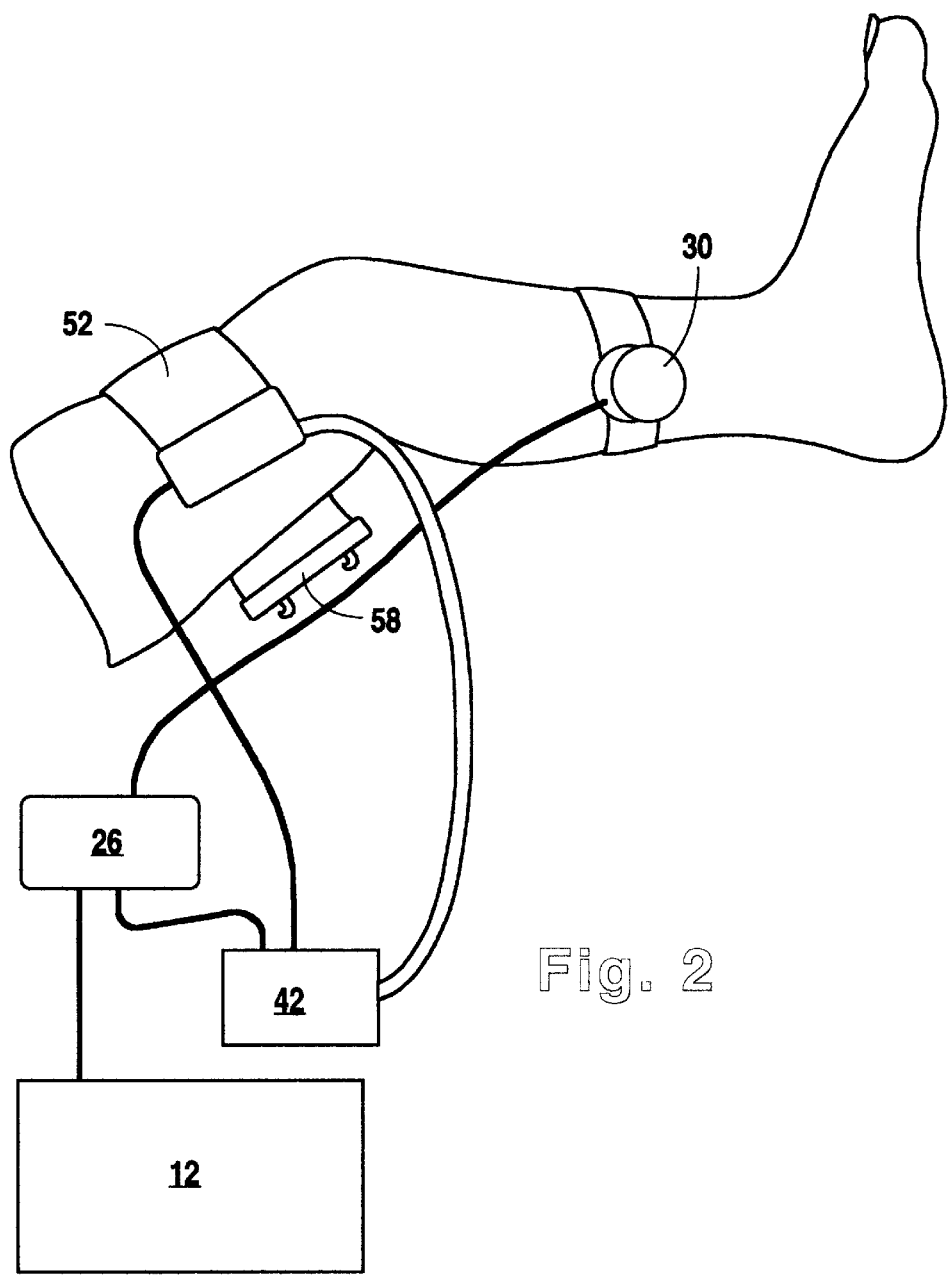

FIG. 2 is a perspective view of an aspect of the present invention.

Figure 3:
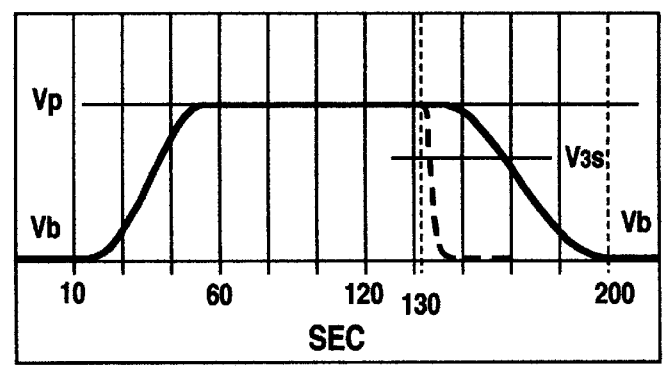

FIG. 3 is a graphical representation of blood volume change in a calf.

Figure 4:
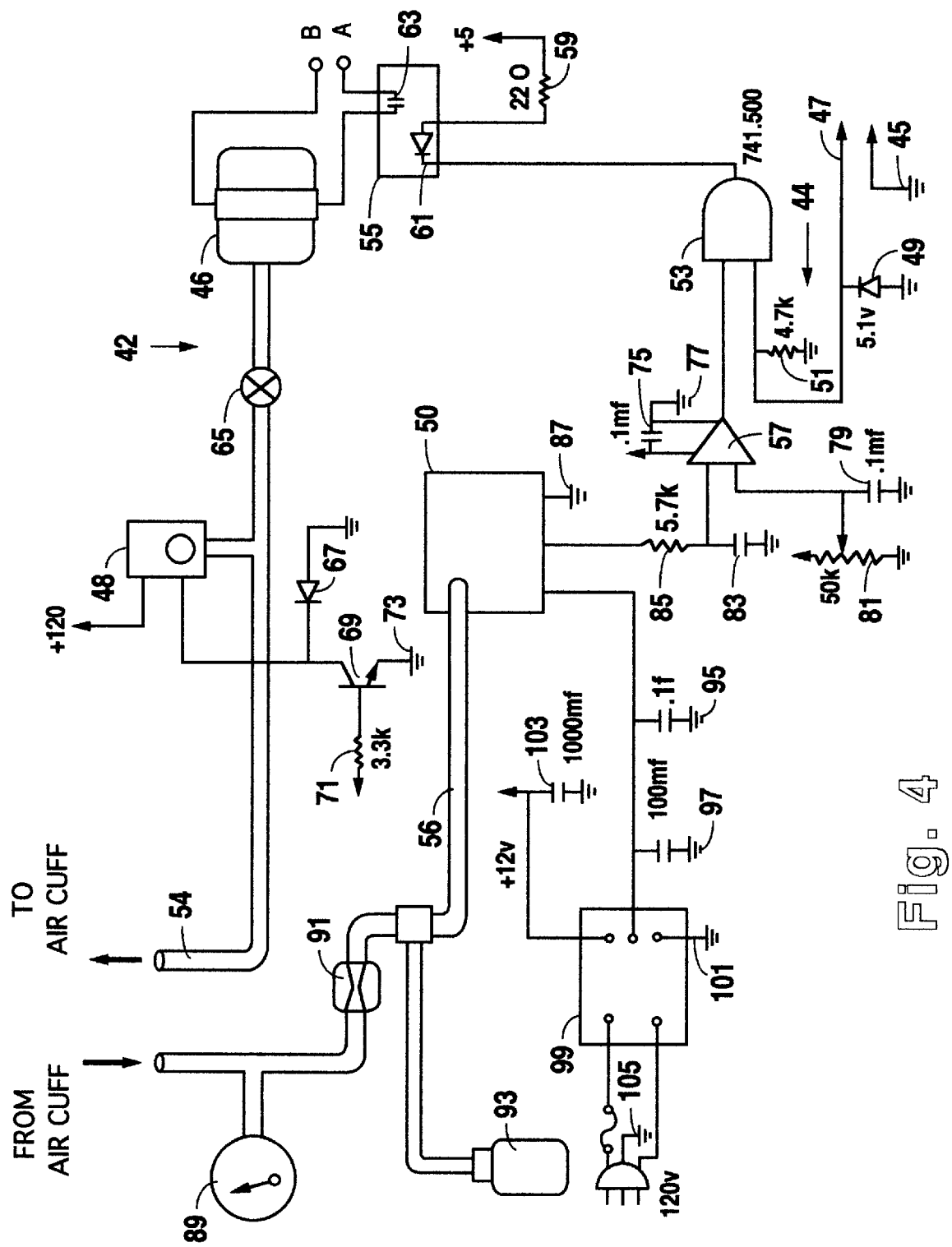

FIG. 4 is a schematic representation of an aspect of the invention.

Figure 5A:
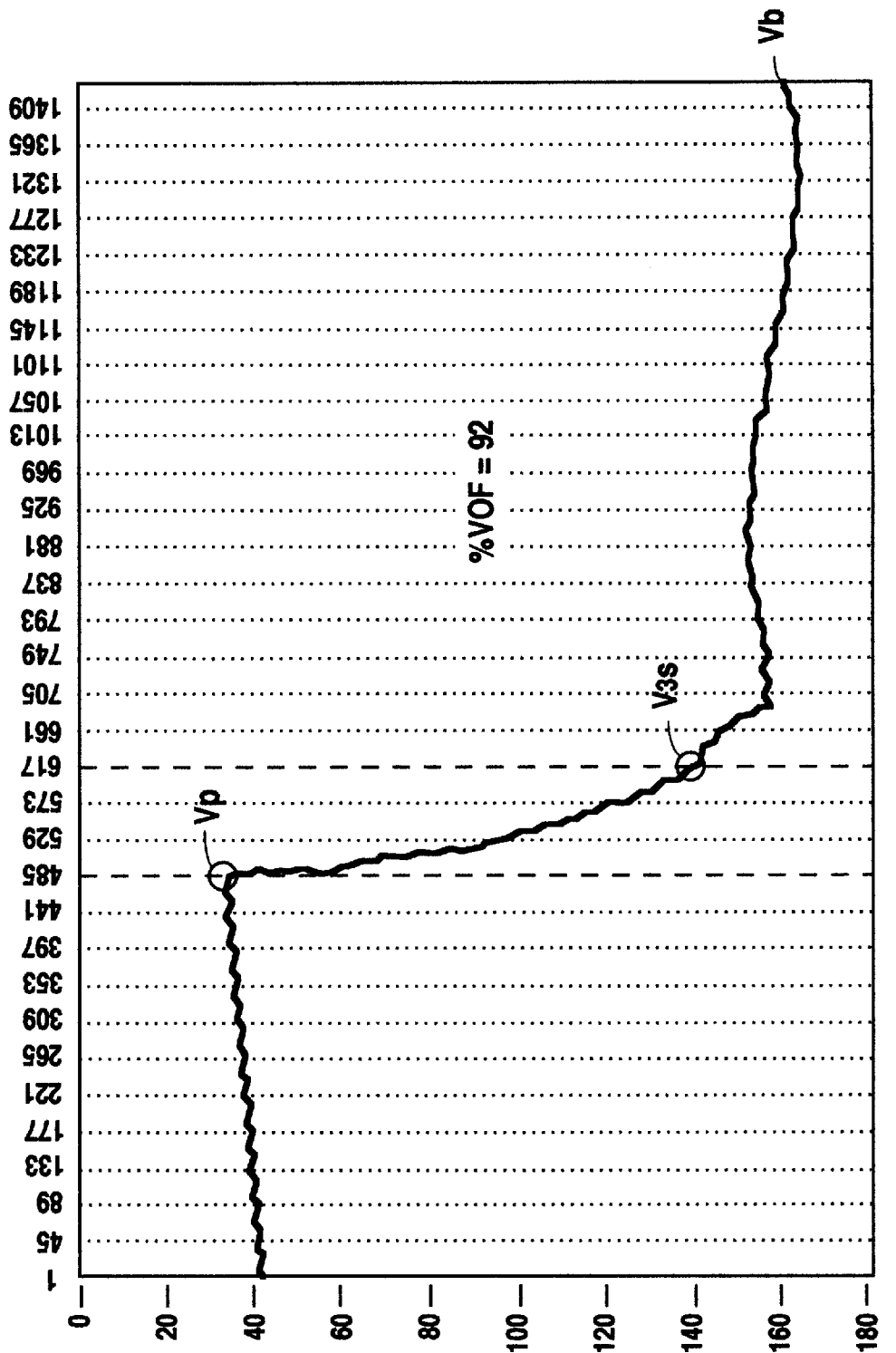

FIG. 5a is another graphical representation of blood volume change in a calf.

FIG. 5b is yet another graphical representation of blood volume change in a calf.

Figures 6, 7:
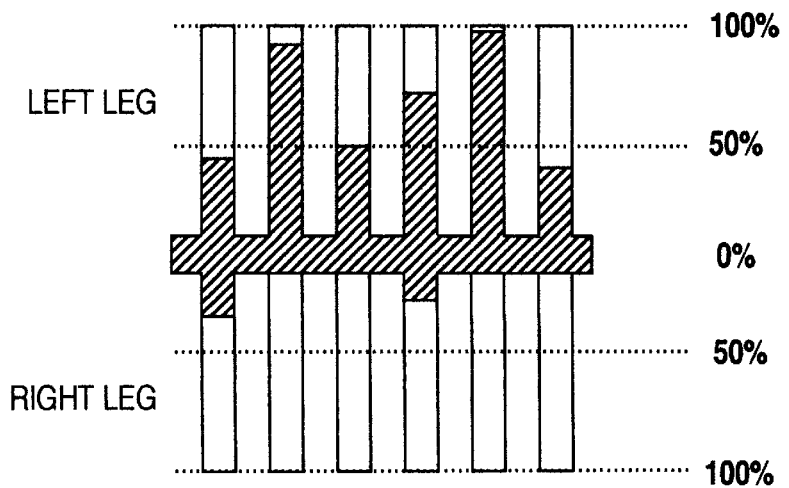

FIG. 6 is a chart of biocharacteristics indicative of DVT.

FIG. 7 is an exemplary graphical representation of the left and the right leg's percent of risk of DVT.

Figure 8:
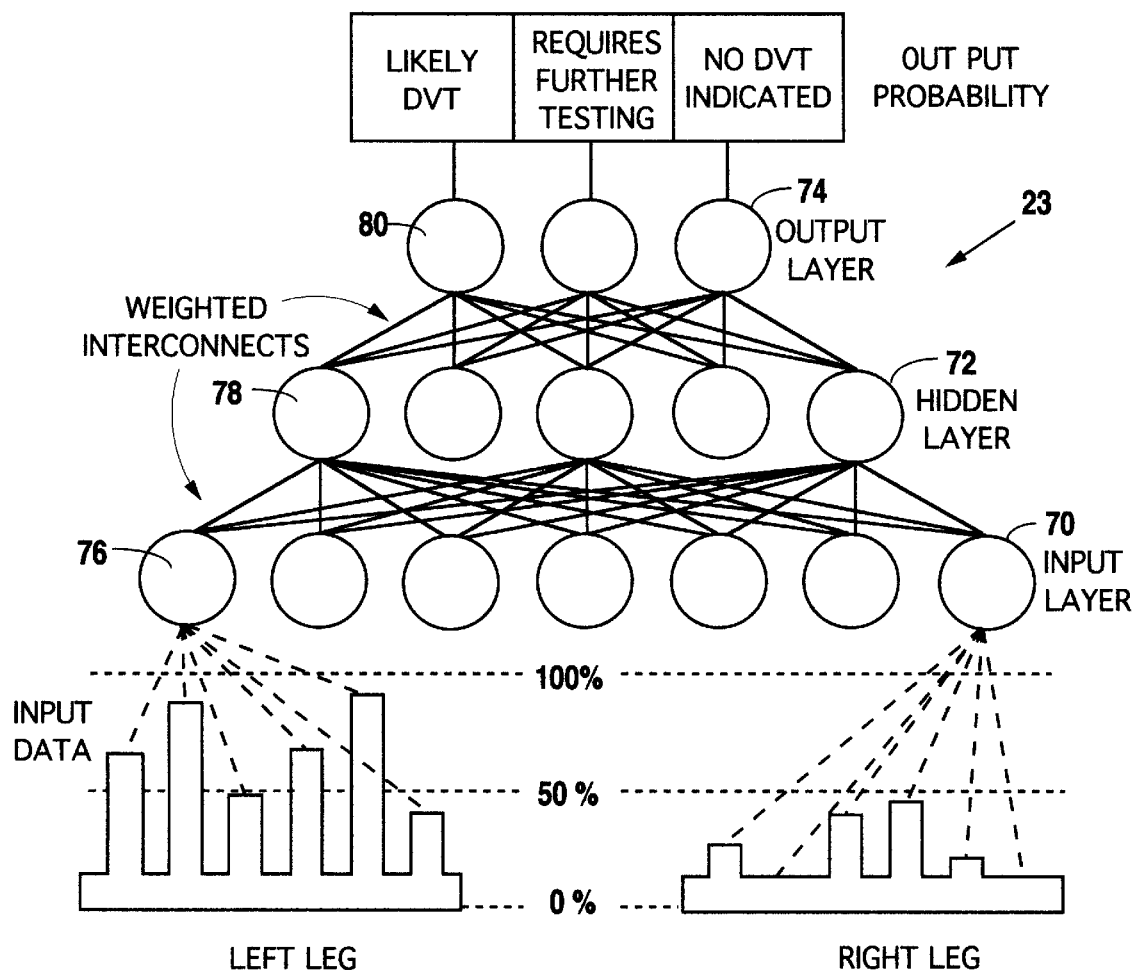

FIG. 8 shows a neural network of the present invention.

Figure 9:
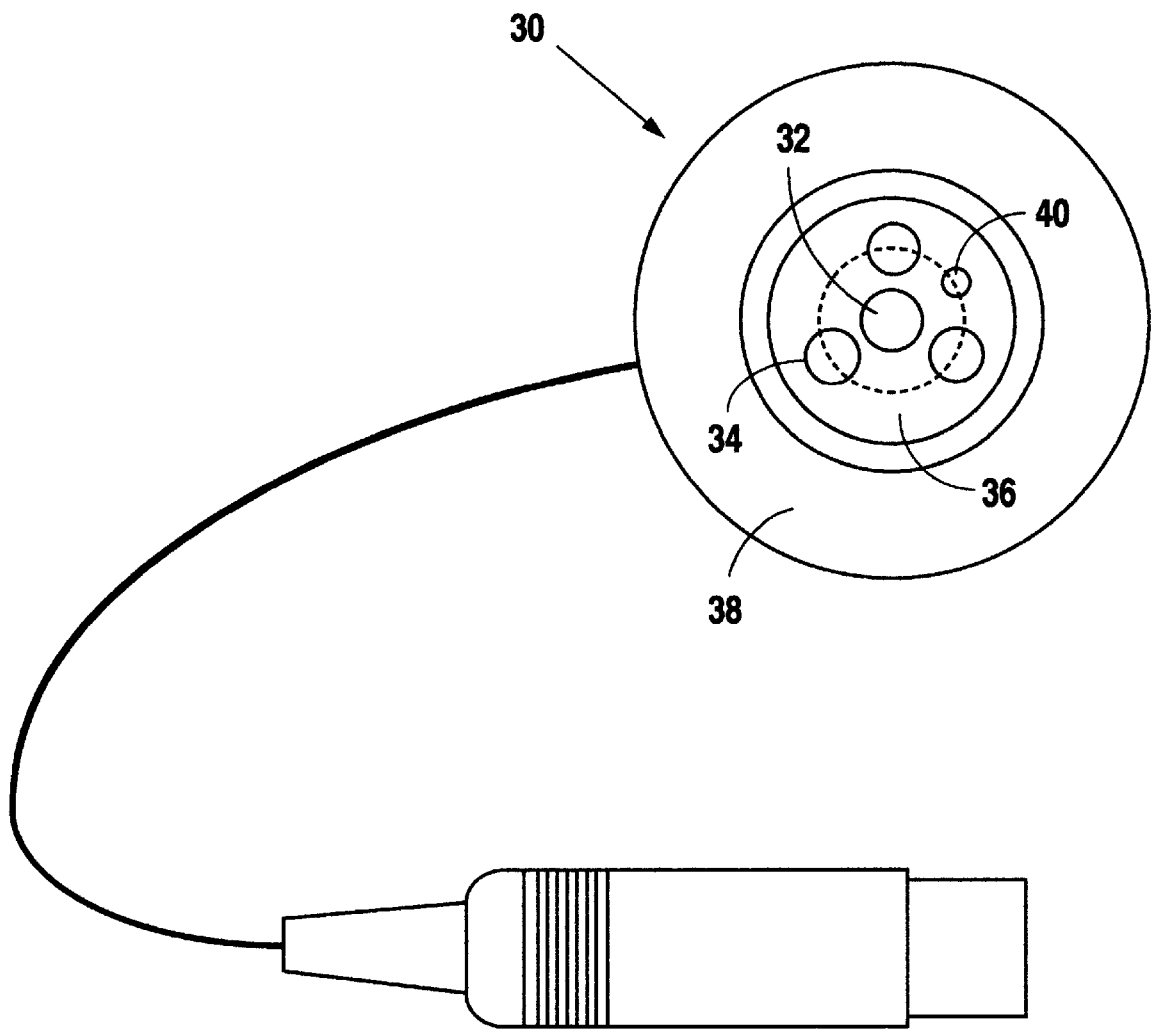

FIG. 9 shows the optical sensor of the present invention for measuring blood volume of the calf.

Figure 10:
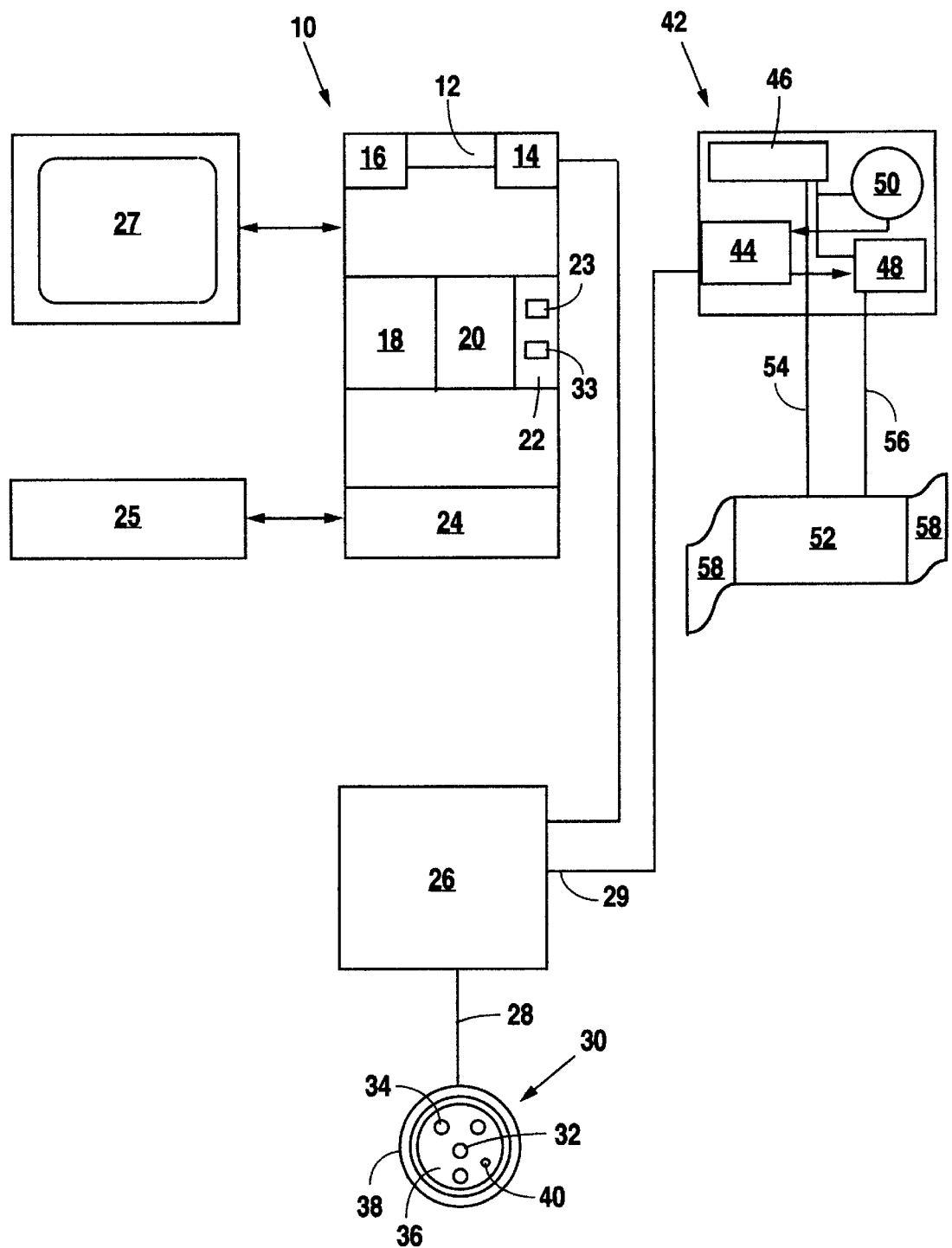

FIG. 10 shows a schematic of the present invention.

DETAILED DESCRIPTION OF THE INVENTION

Referring to the drawings, an apparatus for detecting DVT in a patient of the present invention is generally referred to by the numeral 10. Referring to FIG. 10, the apparatus 10 includes computer 12 having a central processor (CP) 14 (e.g., 486 or Pentium), video card 16 (e.g., a VGA graphics adapter) operably associated with the CP 14, conventional random access memory (RAM) 18, read only memory (ROM) 20 and hard disk memory 22 which are operably associated with the CP 14. The computer 12 has operably associated therewith a risk factor analyzer 33 and neural network 23, the particulars of which are further described hereinafter.

A multiple input/output interface 24 is likewise operably associated with the CP 14. A removable disk storage 25 is provided and operably connected to the multiple input/output interface 24.

A monitor 27 is provided and is operably connected to the video card 16. Preferably, the monitor 27 is of a type such as a LCD monitor having a touch screen capacity.

An analog to digital (A/D) converter 26 is operably connected to the CP 14. The A/D converter includes dual channels (minimum) 16 bit A/D converter characteristics having dual input/output lines 29 and 31.

Figure 1:
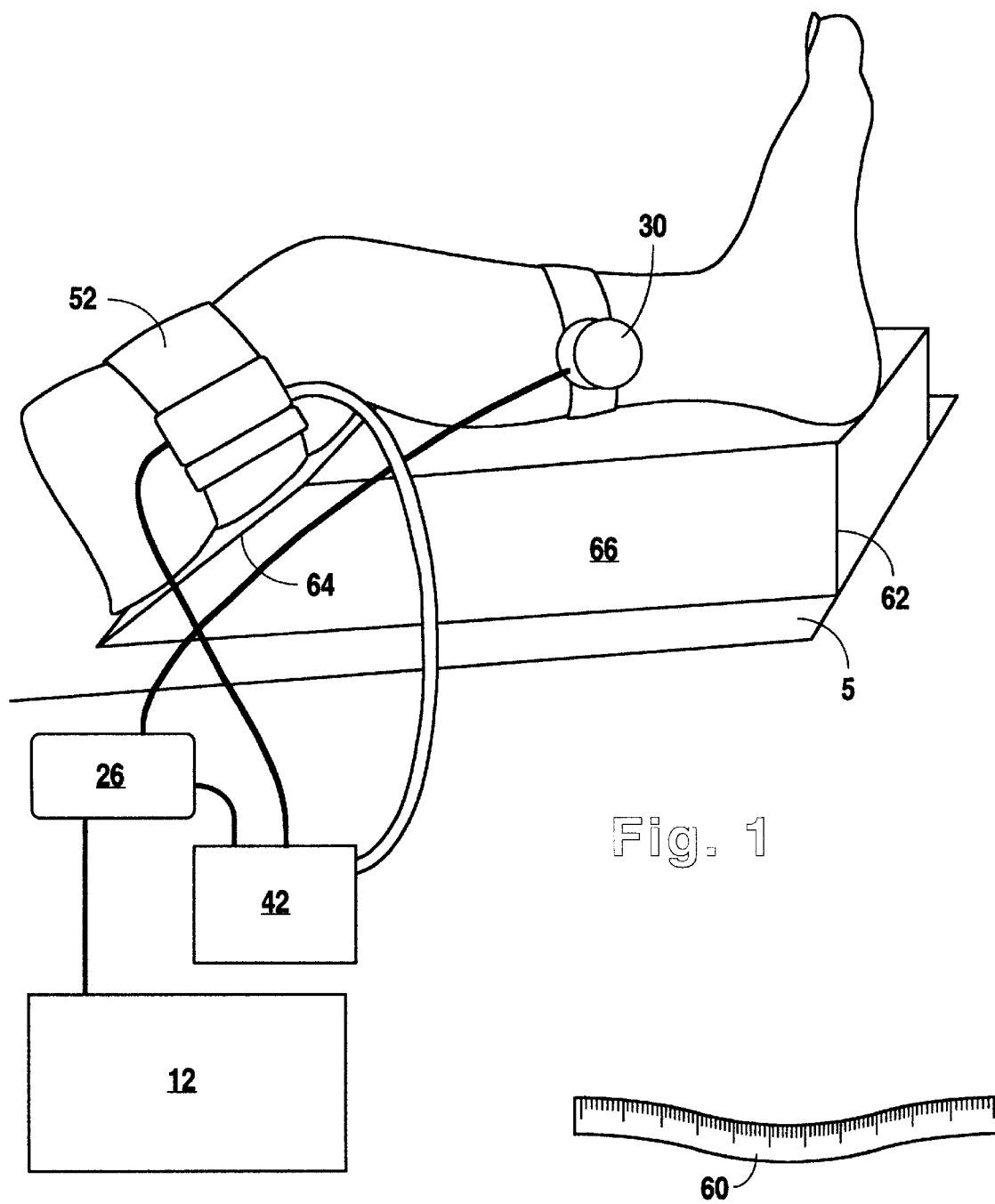
FIG. 1 shows an arrangement of the present invention.

A photo plethysmographic (PPG) sensor 30 is operably connected to the A/D 26. As seen in FIG. 9, the PPG sensor 30 includes a single generally centrally located photo diode (receiver) 32 and three light emitting diodes (LEDs-transmitters) 34 generally equidistantly spaced apart at 120° about and from the photo diode 32. The photo diode 32 and LEDs 34 are operably disposed within a housing 36. A disposable double-sided adhesive collar 38 is provided such that one side is connected to a peripheral surface of the housing 36 adjacent the photo diode 32 and LEDs 34. Another side of the collar 38 is adhesively connectable to a predetermined position on a calf of the patient, preferably on a medial surface of the calf about 10 cm above the malleolus as seen in FIGS. 1 and 2. The PPG 30 uses near infrared light to illuminate the skin to a depth of about 0.5 to 1.5 mm where the light is either absorbed by red blood cells in the microcirculation or reflected back to the photo diode 32. The photo diode 32 and LEDs 34 are set to a wavelength which is optimized for enabling measuring blood volume in the calf, preferably approximately 805 nm has been found suitable. The reflected light is converted into an electrical signal via A/D 26 and used by the computer 12, risk factor analyzer 33 and neural network 23 as later described. The computer 12 includes software for receiving signals and transmitting signals to the monitor 27 in a manner to display the signals as a function of dermal blood volume.

Also, a thermistor (heat sensitive resistor) 40 is also resident and operably disposed in the housing 36 to enable contact thereof with the patient's skin when the collar 38 is connected to the patient's skin. The thermistor 40 enables the measuring of temperature of the patient's skin and generates a converted signal via A/D 26 and is used by the computer 12 as later described.

As generally shown in FIG. 10, a pneumatic system 42 is provided and has a control interface 44 operably connected to the A/D 26. The control interface 44 is operably connected to an air compressor 46, solenoid controlled air vent 48 and solid-state air pressure sensor 50.

More particularly, the pneumatic system 42 is shown in FIG. 4. The control interface 44 includes a control ground signal 45 and a compressor control signal 47. As shown, the compressor control signal 47 has associated therewith a Zener diode 49, resistor 51 and NAND gate 53. Further, the NAND gate 53 is connected to a solid state relay 55 and operational amplifier 57.

The solid state relay 55 has operably associated therewith a resistor 59, diode 61 and triac 63 and is operably connected to the air compressor 46. The air compressor 46 is operably connected to the solenoid controlled air vent 48 via hose 54 which has a check valve 65 disposed therebetween. The solenoid controlled air vent 48 is operably connected to a diode 67, transistor 69, resistor 71 and ground 73.

An inflatable venous occlusion cuff 52 is operably connected to the air compressor 46 and air vent 48 via a detachable hose 54 such that the cuff 52 can be inflated and deflated via the control interface 44. The inflatable cuff 52 is arranged as a generally rectangular bladder of a length and width great enough to substantially encircle or envelop an upper thigh of the patient and has fasteners 58, such as Velcro, to secure one end of the cuff 52 to its other end about the thigh.

The operational amplifier 57 has operably associated therewith a capacitor 75 and ground 77 and is further connected to capacitor 79 and resistor 81 and capacitor 83 and resistor 85. The resistor 85 connects to the pressure sensor 50 having a ground 87 and which is connected to the cuff 52 via a detachable hose 56. Operably interposed in the hose 56 between the cuff 52 and pressure sensor 50 is a pressure gauge 89, flow restrictor 91 and pneumatic accumulator 93.

The pressure sensor 50 has operably connected thereto capacitors 95 and 97 which connect to a power supply 99. The power supply 99 has a ground 101, capacitor 103 and conventional electrical line 105.

Figure 1A:
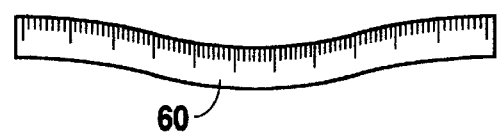

The apparatus 10 further incorporates the use of a tape measure 60 as seen in FIG. 1a for measuring calf size. The calf size is utilized by the computer 12 as described hereinafter for determining risk of DVT.

FIG. 1 shows a wedge shaped foam pillow 62 of a sufficient length for the patient to place and support a leg thereon during the method of detecting DVT described herein. The pillow 62 is provided with a section 64 being inclined, preferably at about 25° to 30°, from a generally planar support surface 5 and extending from about a rear end to about a back of the knee of the patient. A portion 66 supports a remainder of the leg from the knee to a foot in a relatively parallel spaced relation to the support surface 5. The design of the pillow 62 is such that the patient's leg is raised above the heart while maintaining the knee in a flexed position in order to relax the popliteal space of the leg.

A risk factor analyzer 33 which is resident in and utilized by the computer 12 to aid in the generating of output indicative of DVT is receptively connected to sensors 30, 40 and 50. The monitor 27 via the computer 12 provides a visual aid to observe the various output signals described herein, such as cuff pressure, blood volume, temperature, calf size and physiological condition and individual risk factors associated with the aforementioned biocharacteristics. The risk factor analyzer 33 is composed of a series of "fuzzy" rules stored in the CP 14 which are applied to each of the aforementioned biocharacteristics for evaluation of overall risk for DVT. If a particular biocharacteristic such as venous outflow percent falls within the boundaries of its corresponding rule, the risk factor for said biocharacteristic is low. If, on the other hand, the biocharacteristic falls outside the boundary of its corresponding rule, the risk factor for that said biocharacteristic is high. Each of the risk factors associated with its corresponding biocharacteristic is stored in the random access memory 18 of the CP 14 for subsequent analysis by the neural network 23.

As shown in FIG. 8, the neural network 23 includes at least one layer of trained neuron-like units, and preferably at least three layers. The neural network 23 includes input layer 70, hidden layer 72, and output layer 74. Each of the input layer 70, hidden layer 72, and output layer 74 include a plurality of trained neuron-like units 76, 78 and 80, respectively.

Neuron-like units 76 can be in the form of software or hardware. The neuron-like units 76 of the input layer 70 include a receiving channel for receiving a sensed signal, wherein the receiving channel includes a predetermined modulator for modulating the signal.

The neuron-like units 78 of the hidden layer 72 are individually receptively connected to each of the units 76 of the input layer 70. Each connection includes a predetermined modulator for modulating each connection between the input layer 70 and the hidden layer 72.

The neuron-like units 80 of the output layer 74 are individually receptively connected to each of the units 78 of the hidden layer 72. Each connection includes a predetermined modulator for modulating each connection between the hidden layer 72 and the output layer 74. Each unit 80 of said output layer 74 includes an outgoing channel for transmitting the output signal.

Each trained neuron-like unit includes a dendrite-like unit, and preferably several, for receiving incoming signals. Each dendrite-like unit includes a particular modulator which modulates the amount of weight which is to be given to the particular characteristic sensed as described below. In the dendrite-like unit, the modulator modulates the incoming signal and subsequently transmits a modified signal. For software, the dendrite-like unit comprises an input variable $X_a$ and a weight value $W_a$ wherein the connection strength is modified by multiplying the variables together. For hardware, the dendrite-like unit can be a wire, optical or electrical transducer having a chemically, optically or electrically modified resistor therein.

Each neuron-like unit includes a soma-like unit which has a threshold barrier defined therein for the particular characteristic sensed. When the soma-like unit receives the modified signal, this signal must overcome the threshold barrier whereupon a resulting signal is formed. The soma-like unit combines all resulting signals and equates the combination to an output signal indicative of one of a proximal DVT, necessitating further testing for proximal DVT and absence of proximal DVT.

For software, the soma-like unit is represented by the sum $\alpha=\Sigma_a X_a W_a - \beta$, where $\beta$ is the threshold barrier. This sum is employed in a Nonlinear Transfer Function (NTF) as defined below. For hardware, the soma-like unit includes a wire having a resistor; the wires terminating in a common point which feeds into an operational amplifier having a nonlinear component which can be a semiconductor, diode, or transistor.

The neuron-like unit includes an axon-like unit through which the output signal travels, and also includes at least one bouton-like unit, and preferably several, which receive the output signal from the axon-like unit. Bouton/dendrite linkages connect the input layer to the hidden layer and the hidden layer to the output layer. For software, the axon-like unit is a variable which is set equal to the value obtained through the NTF and the bouton-like unit is a function which assigns such value to a dendrite-like unit of the adjacent layer. For hardware, the axon-like unit and bouton-like unit can be a wire, an optical or electrical transmitter.

The modulators of the input layer modulate the amount of weight to be given the preprocessed biocharacteristics such as:

temperature risk factor as determined from the thermistor 40 at predetermined times as described above;

blood outflow percent risk factor as determined by the CP 14 as a function of the ratio of the change in blood volume in a predetermined time (e.g., three seconds) after relaxing cuff 52 with respect to the amount of venous capacity;

tissue condition and size risk factors as observed input;

age risk factor as observed input; and pain felt by the patient as observed input using "Homan's Sign" risk factor scaled from 1–10.

For example, if a patient's blood outflow percent risk factor is higher than, lower than, or in accordance with what has been predetermined as normal, the soma-like unit would account for this in its output signal and bear directly on the neural network's output which is indicative of the likelihood of proximal DVT and accordingly the need for further treatment and/or testing. The modulators of the output layer modulate the amount of weight to be given for each characteristic indicating one of a proximal DVT, necessitating further testing for proximal DVT and absence of proximal DVT. It is not exactly understood what weight is to be given to characteristics which are modified by the modulators of the hidden layer, as these modulators are derived through a training process defined below.

The training process is the initial process which the neural network must undergo in order to obtain and assign appropriate weight values for each modulator. Initially, the modulators and the threshold barrier are assigned small random non-zero values. The modulators can each be assigned the same value but the neural network's learning rate is best maximized if random values are chosen. Empirical input data are fed in parallel into the dendrite-like units of the input layer and the output observed.

The Nonlinear Transfer Function (NTF) employs $\alpha$ in the following equation to arrive at the output:

$$NTF = \frac{1}{[1 + e^{-\alpha}]}$$

For example, in order to determine the amount weight to be given to each modulator for temperature differential risk factor, the NTF is employed as follows:

If the NTF approaches 1, the soma-like unit produces an output signal indicating a proximal DVT. If the NTF is within a predetermined range about 0.5, the soma-like unit produces an output signal indicating further testing for DVT is needed. If the NTF approaches 0, the soma-like unit produces an output signal indicating no proximal DVT.

If the output signal clearly conflicts with the known empirical output signal, an error occurs. The weight values of each modulator are adjusted using the following formulas so that the input data produces the desired empirical output signal.

For the output layer:

$W^*_{kol} = W_{kol} + GE_k Z_{kos}$ $W^*_{kol}$=new weight value for neuron-like unit k of the outer layer.

$W_{kol}$=current weight value for neuron-like unit k of the outer layer.

G=gain factor $Z_{kol}$=actual output signal of neuron-like unit k of output layer.

$D_{kos}$=desired output signal of neuron-like unit k of output layer.

$E_k = Z_{kos}(1-Z_{kos})(D_{kos}-Z_{kos})$, (this is an error term corresponding to neuron-like unit k of outer layer). For the hidden layer:

$W^*_{jhl} = W_{jhl} + GE_j Y_{jos}$ $W^*_{jhl}$=new weight value for neuron-like unit j of the hidden layer.

$W_{jhl}$=current weight value for neuron-like unit j of the hidden layer.

G=gain factor $Y_{jos}$=actual output signal of neuron-like unit j of hidden layer.

$E_j = Y_{jos}(1-Y_{jos})E_k(E_{k^*}W_{kol})$, (this is an error term corresponding to neuron-like unit j of hidden layer over all k units).

For the input layer:

$W^*_{iil} = W_{iil} + GE_i X_{ios}$ $W^*_{iil}$=new weight value for neuron-like unit I of input layer.

$W_{iil}$=current weight value for neuron-like unit I of input layer.

G=gain factor $X_{ios}$=actual output signal of neuron-like unit I of input layer.

$E_i = X_{ios}(1-X_{ios})E_j(E_{j*}W_{jhl})$, (this is an error term corresponding to neuron-like unit i of input layer over all j units).

The training process consists of entering new (or the same) empirical data into neural network 23 as the input data is repeated and the output signal observed. If the output is again in error with what the known empirical output signal should be, the weights are adjusted again in the manner described above. This iterative process continues until the output signals are substantially in accordance with the desired (empirical) output signal, then the weight of the modulators are fixed.

Upon fixing the weights of the modulators, predetermined solution space memory indicative of a proximal DVT, necessitating further testing for proximal DVT and absence of proximal DVT are established. The neural network is then trained and can make generalizations about input data by projecting input data into solution space memory which most closely corresponds to that data.

As seen in FIG. 8, the individual risk factors derived by risk factor analyzer 33, and associated with each corresponding biocharacteristic described herein above, are provided as inputs to the neural network 23 which subsequently generates a signal in response thereto. Observed input as previously described may be entered into the risk factor analyzer 33 via the touch sensitive screen of monitor 27.

The preferred method of DVT detection begins with soliciting patient information prompted by the computer 12 via the monitor 27. The patient's name, age, limbs to be evaluated (i.e., left and right legs) and other clinical indications are entered into the computer 12 for use by the risk factor analyzer 33 and neural network 23.

The patient is placed in a supine position and is conventionally tested via extending the leg and manually conducting dorsiflexion of the foot and entering into the computer 12 a number from zero to 10, zero representing no pain and 10 representing severe pain. This is commonly referred to as a "Homan's Sign" and this value would be used by the risk factor analyzer 33 and neural network 23.

Using the tape measure 60, a first metric calf size is obtained and entered into the computer 12 for use by risk factor analyzer 33. The PPG sensor 30 along with the thermistor sensor 40 are connected to a prepared medial surface of the patient's calf approximately 10 cm above the malleolus such that the thermistor sensor 40 is in contact with the skin.

On the same leg, the cuff 52 is placed about the patient's thigh in as high a position as possible and the Velcro fasteners 58 are connected such that the cuff 52 envelopes the thigh in a relatively loose manner to prevent the cuff 52 from impeding nominal venous blood flow. The hoses 54 and 56 are connected to the cuff 52.

The wedge shaped foam pillow 62 is disposed beneath the leg as shown in FIG. 1. The leg is generally disposed at about 25° to 30° angle elevated above the heart to enable blood to freely flow from the distal deep and superficial venous system to the heart. Using the touch screen of the monitor 27, the computer 12 is initiated to begin evaluation wherein resident software determines and monitors the slope of temperature drift from signals received from the PPG sensor 30. The PPG sensor 30 is initiated by the computer 12 upon detection of the PPG sensor 30 equilibrating to the patient's skin temperature. At this point, a first temperature taken from thermistor sensor 40, is stored by the computer resident software in random access memory 18 as a baseline resting temperature for subsequent use by the risk factor analyzer 33 and neural network 23.

Referring to FIG. 3, a baseline reading of the blood volume (Vb) is obtained by averaging signals generated from the PPG sensor 30 over a sufficient period (typically several seconds). The computer 12 then initiates compressor 46 to cause pneumatic inflation of the cuff 52. The pressure sensor 50 detects when the cuff 52 has reached a predetermined pressure which occludes the deep and superficial veins while permitting arterial flow, preferably about 55 mm Hg, whereafter the computer 12 shuts off the compressor 46. In this way, blood can enter the calf through the arteries but cannot return to the heart through the veins. Changes in pressure of the cuff 52 caused by stretching, for example, will be detected by the pressure sensor 50 relayed to the computer 12 via a control loop between the compressor 46 and pressure sensor 50 and will cause inflation or deflation of the cuff 52 as required to maintain the desired pressure.

Pressure is maintained for a predetermined period of time to permit arterial blood flow to plateau and calf blood volume to stabilize. This can take about 120 seconds. At this point, the venous system is substantially filled and a second peak blood volume (Vp) is obtained in a like manner as previously described. Also, a second temperature is obtained via the thermistor sensor 40 and stored by the computer 12 for use by the risk factor analyzer 33 and neural network 23.

After these performed functions, the computer 12 initiates the opening of the solenoid controlled air vent 48 to release the pneumatic pressure within the cuff 52. The veins which were occluded are opened to permit unimpeded blood flow therethrough back to the heart. The blood volume (V3s) is again measured after a period which has been predetermined to be adequate for screening for DVT, preferably about three seconds (3s). The solenoid controlled air vent 48 remains open until the Vb is again reached.

The computer 12 calculates the ratio of change in blood volume (Vp-V3s) in the first three seconds with respect to the amount of venous capacity (Vp-Vb), i.e., (Vp-V3s)/(Vp-Vb) otherwise stated as the percent of venous outflow %VOF. The %VOF is stored by the computer 12 and utilized by the risk factor analyzer 33 and neural network 23. FIG. 5a shows a relatively high %VOF providing an indicium of absence of DVT whereas FIG. 5b shows a relatively low %VOF providing an indicium of the suspected presence of DVT.

A final temperature reading is obtained via thermistor sensor 40 and stored by the computer 12 and utilized by the risk factor analyzer 33 and neural network 23. In a like manner, these data inputs are determined and stored for the other leg of the patient so that a comparison can be made between the legs. These data inputs are illustrated in an exemplary manner in the chart of FIG. 6. FIG. 7 illustrates the percent risk factor for each of the right and left legs as determined by the risk factor analyzer 33 based on its pre-programmed rules.

After each risk factor corresponding with the individual above described biocharacteristics has been tabulated and stored by the risk factor analyzer 33, the neural network 23 provides the overall determination as to the presence or absence of DVT as depicted in FIG. 8. The risk factors are provided to the input layer 70 of neural network 23 as a numerical value between zero and one, scaled to represent corresponding risk indication from between zero and 100 percent, whereas 0.5 would be representative of a risk indication of 50 percent.

The above described embodiments are set forth by way of example and are not for the purpose of limiting the present invention. It will be readily apparent to those skilled in the art that obvious modifications, derivations and variations can be made to the embodiments without departing from the scope of the invention. Accordingly, the claims appended hereto should be read in their full scope including any such modifications, derivations and variations.

What is claimed is:

1. An apparatus for detecting deep vein thrombosis (DVT) in a patient, said apparatus comprising:
   an automated system for generating an output indicative of DVT, said automated system being adapted to manipulate biocharacteristic signals to arrive at the output indicative of DVT;
   a first biocharacteristic gathering device operably associated with said automated system for providing said automated system with a first biocharacteristic signal, said first biocharacteristic gathering device being a photo-plethysmographic device adapted to be placed at a predetermined position on a calf of the patient for measuring blood volume, the first biocharacteristic signal being a blood volume signal from said photo-plethysmographic device;
   a second biocharacteristic gathering device operably associated with said automated system for providing said automated system with a second biocharacteristic signal; and
   said automated system comprising a multiple risk factor analyzer, said multiple risk factor analyzer being adapted to perform a weighted analysis of the first and second biocharacteristic signals to arrive at the output indicative of DVT.

2. The apparatus for detecting DVT as recited in claim 1, wherein said multiple risk factor analyzer comprises a neural network.

3. The apparatus for detecting DVT as recited in claim 1, said apparatus further comprising a cuff adapted to produce a controlled occlusion of the deep and superficial veins of the patient's leg.

4. The apparatus for detecting DVT as recited in claim 3, wherein said cuff is operable by said automated system to produce the controlled occlusion of the deep and superficial veins of the patient's leg for a determinable time period.

5. The apparatus for detecting DVT as recited in claim 4, wherein said automated system is adapted to retrieve the first biocharacteristic signal from said first biocharacteristic gathering device prior to said determinable time period and repeatedly during said determinable time period.

6. The apparatus for detecting DVT as recited in claim 5, wherein said risk factor analyzer is adapted to perform the weighted analysis of the first and second biocharacteristic signals with reference to time.

7. The apparatus for detecting DVT as recited in claim 6, wherein said second biocharacteristic gathering device comprises a temperature measurement device adapted to determine the temperature of the patient's calf as the second biocharacteristic signal.

8. The apparatus for detecting DVT as recited in claim 6, wherein said second biocharacteristic gathering device comprises a size measurement device adapted to determine the size of the patient's calf as the second biocharacteristic signal.

9. The apparatus for detecting DVT as recited in claim 8, said apparatus further comprising a manual entry system for manually reporting the second biocharacteristic signal to said automated system.

10. The apparatus for detecting DVT as recited in claim 9, wherein said manual entry system comprises a touch screen display.

11. An apparatus for detecting deep vein thrombosis (DVT) in a patient's leg, said apparatus comprising:
    an automated system for generating an output indicative of DVT in the patient's leg, said automated system being adapted to manipulate biocharacteristic signals to arrive at the output indicative of DVT;
    a first biocharacteristic gathering device operably associated with said automated system for providing said automated system with a first biocharacteristic signal from the patient's leg;
    a second biocharacteristic gathering device operably associated with said automated system for providing said automated system with a second biocharacteristic signal from the patient's leg; and
    said automated system comprising a multiple risk factor analyzer, said multiple risk factor analyzer being adapted to perform a weighted analysis of the first and second biocharacteristic signals to arrive at the output indicative of DVT.

12. The apparatus for detecting DVT as recited in claim 11, wherein said multiple risk factor analyzer comprises a neural network.

13. The apparatus for detecting DVT as recited in claim 12, wherein said neural network is trained to perform a relative evaluation of the first and second biocharacteristic signals to arrive at an assessment of the patient's overall risk for DVT.

14. The apparatus for detecting DVT as recited in claim 13, wherein said first biocharacteristic gathering device comprises a blood volume measurement device.

15. The apparatus for detecting DVT as recited in claim 14, wherein said second biocharacteristic gathering device comprises a calf temperature measurement device.

16. A method for detecting deep vein thrombosis (DVT) in a patient's leg, said method comprising the steps of:
    obtaining a first biocharacteristic signal and a second biocharacteristic signal, said first biocharacteristic signal and said second biocharacteristic signal each being indicative of blood flows in the patient's leg;
    producing a controlled occlusion of the deep and superficial veins of the patient's leg such that blood volume in the patient's leg is substantially maximized;
    eliminating said controlled occlusion of the deep and superficial veins of the patient's leg to allow natural flows of blood from the patient's leg;
    re-obtaining said first biocharacteristic signal and said second biocharacteristic signal during the period of natural flows following said eliminating said controlled occlusion step; and
    performing a weighted analysis over time of said first biocharacteristic signal and said second biocharacteristic signal to arrive at an assessment of the patient's DVT status.

17. The method for detecting DVT as recited in claim 16, wherein said performing a weighted analysis step comprises utilizing a neural network to balance known DVT risk factors.

18. The method for detecting DVT as recited in claim 17, wherein said known DVT risk factors comprise abnormal venous emptying.

19. The method for detecting DVT as recited in claim 18, wherein said known DVT risk factors further comprise abnormal leg temperature changes.

20. The method for detecting DVT as recited in claim 18, wherein said known DVT risk factors further comprise abnormal leg size changes.

21. The method for detecting DVT as recited in claim 16, wherein said first biocharacteristic signal is obtained by a photo-plethysmographic device.

22. The method for detecting DVT as recited in claim 21, wherein said controlled occlusion is produced by inflating a cuff, said cuff being adapted to produce an occluding pressure at a thigh portion of the patient's leg.

23. The method for detecting DVT as recited in claim 22, wherein said obtaining a first biocharacteristic signal and a second biocharacteristic signal step is conducted under the control of an automated system, said automated system being adapted to further control the inflation of said cuff.

\* \* \* \* \*